(12) United States Patent
Anderson et al.

(10) Patent No.: US 7,455,813 B2
(45) Date of Patent: Nov. 25, 2008

(54) COMPACT ANALYTE TESTING CASSETTE WITH TRUE POSITIVE AND NEGATIVE ANALYTE CONTROLS

(75) Inventors: David Anderson, San Diego, CA (US); Hsaioho Edward Tung, San Diego, CA (US); Haipeng Hu, Hangzhou (CN); Yuchang Wu, Hangzhou (CN)

(73) Assignee: Oakville Hong Kong Co., Limited, Central (HK)

( * ) Notice: Subject to any disclaimer, the term of this patent is extended or adjusted under 35 U.S.C. 154(b) by 0 days.

(21) Appl. No.: 10/890,544

(22) Filed: Jul. 12, 2004

(65) Prior Publication Data

US 2005/0008538 A1 Jan. 13, 2005

Related U.S. Application Data

(60) Provisional application No. 60/486,372, filed on Jul. 11, 2003.

(51) Int. Cl.
*G01N 33/48* (2006.01)
(52) U.S. Cl. .................................. 422/58; 422/61

(58) Field of Classification Search .............. 422/56, 422/58, 61, 99, 102, 104; 436/164, 166, 436/169
See application file for complete search history.

(56) References Cited

U.S. PATENT DOCUMENTS

| | | | | |
|---|---|---|---|---|
| 3,992,158 | A | * | 11/1976 | Przybylowicz et al. ........ 422/57 |
| 4,365,970 | A | * | 12/1982 | Lawrence et al. ............. 436/66 |
| 4,541,987 | A | * | 9/1985 | Guadagno .................... 422/56 |
| 4,826,759 | A | * | 5/1989 | Guire et al. .................... 435/4 |
| 5,648,274 | A | | 7/1997 | Chandler |
| 5,976,895 | A | * | 11/1999 | Cipkowski .................. 436/518 |
| 6,046,058 | A | * | 4/2000 | Sun ............................. 436/514 |

* cited by examiner

*Primary Examiner*—Lyle A Alexander
(74) *Attorney, Agent, or Firm*—Fred C. Hernandez; Mintz, Levin, Cohn, Ferris, Glovsky and Popeo, P.C.

(57) ABSTRACT

The present disclosure includes but is not limited to an assay or test device, such as an immunological assay device, with positive and negative controls for each analyte of interest. In general, the device has a bi-fold, tri-fold or quarter-fold cassette, each folded side having one or more test strips contained therein. The device is compact and easily used by the worker. The present device is particularly useful in a clinical drug of abuse testing setting, in which the use of internal quality controls is regulated by the USCMS and the College of American Pathologists. In addition, the present device provides the advantages of ease of use, small size and reduced cost compared to other devices currently available on the market.

20 Claims, 8 Drawing Sheets

COMPACT ANALYTE TESTING CASSETTE WITH TRUE POSITIVE AND NEGATIVE ANALYTE CONTROLS

CROSS-REFERENCE TO A RELATED APPLICATION

This application claims priority of previously filed U.S. Provisional Patent Application Ser. 60/486,372 filed Jul. 11, 2003. The disclosure of the provisional application is incorporated herein by reference.

BACKGROUND

The disclosure relates generally to the field of sample assaying devices, which can be used to manipulate samples, including samples used to assay for analytes, especially drugs of abuse, antibodies, antigens and biological moieties such as steroids and glucose. In particular, the disclosure relates to improvements in assay device design that provide and true positive and negative control for each analyte of interest, to be used in a clinical setting.

In the drug of abuse testing industry, various governmental agencies and professional organizations, such as but not limited to CLIA, CAP, COLA and JCCHO, have initiated regulations to ensure quality control and standardization of testing with point of care devices. For example, these agencies and organizations may require certain positive, negative or procedural controls to be run at the beginning of the day, or the beginning of a new lot of devices. No point of care test devices currently on the market have true positive and negative controls, to which the test results obtained with the test sample can be compared, creating an ongoing and existing need.

SUMMARY

As a non-limiting introduction to the breath of the present disclosure, the present disclosure includes several general and useful aspects, including:

A device for detecting the presence of an analyte of interest in a sample of a subject in need there of, comprising: a sample test strip, for assaying for the presence or absence of an analyte of interest in an aliquot of the sample of the subject; a positive control, comprising at least one test strip and a positive control solution further comprising the analyte of interest and a buffer; and a negative control, comprising at least one test strip and a negative control solution further comprising a buffer; wherein said positive and negative controls indicate the correct functioning of the assay for the analyte of interest.

A method for detecting an analyte of interest in a sample of a subject in need there of, comprising: providing a sample of the subject; providing the test device of claim 1 or claim 9, applying an aliquot of said sample to said sample test strip; applying an aliquot of said positive control solution to said positive control test strip; applying an aliquot of said negative control solution to said negative control test strip; incubating said test device; reading said test results and said positive and negative control results; and confirming the correct functioning of said test device by comparing said test results to said positive and said negative control results.

A kit for testing a sample for the presence of an analyte, comprising: the test device of the present disclosure, positive and negative control solutions, and instructions for the use of the test device and the control solutions.

The present disclosure includes, but is not limited to, an assay device able to detect or measure, for example, chemically or immunologically, analytes in a fluid sample, especially those assay devices with positive and negative controls. In particular, the assay device may be used to detect or measure drugs of abuse in a fluid sample, especially a biological fluid sample, such as urine or blood, collected from a subject in need of testing.

The present disclosure includes a variety of other useful aspects, which are detailed herein. These aspects of the disclosure can be achieved by using the articles of manufacture and compositions of matter described herein. To gain a full appreciation of the scope of the present disclosure, it will be further recognized that various aspects of the present devices and methods can be combined to make desirable embodiments. In addition, a variety of other aspects and embodiments of the present disclosure are described herein.

BRIEF DESCRIPTION OF THE DRAWINGS

The foregoing summary, as well as the following detailed description may be better understood when read in conjunction with the accompanying drawings, which are incorporated in and form a part of the specification. The drawings serve to explain the principles of the invention and illustrate embodiments of the present invention that are preferred at the time the application was filed. It should be understood, however, that the invention is not limited to the precise arrangements and instrumentalities shown.

The accompanying drawings, which are incorporated in and form a part of the specification, illustrate the embodiments of the present invention and, together with the following description, serve to explain the principles of the invention. For the purpose of illustrating the invention, there are shown in the drawings embodiments which are presently preferred, it being understood, however, that the invention is not limited to the specific instrumentality or the precise arrangement of elements or process steps disclosed.

In the drawings:

Figure 1:
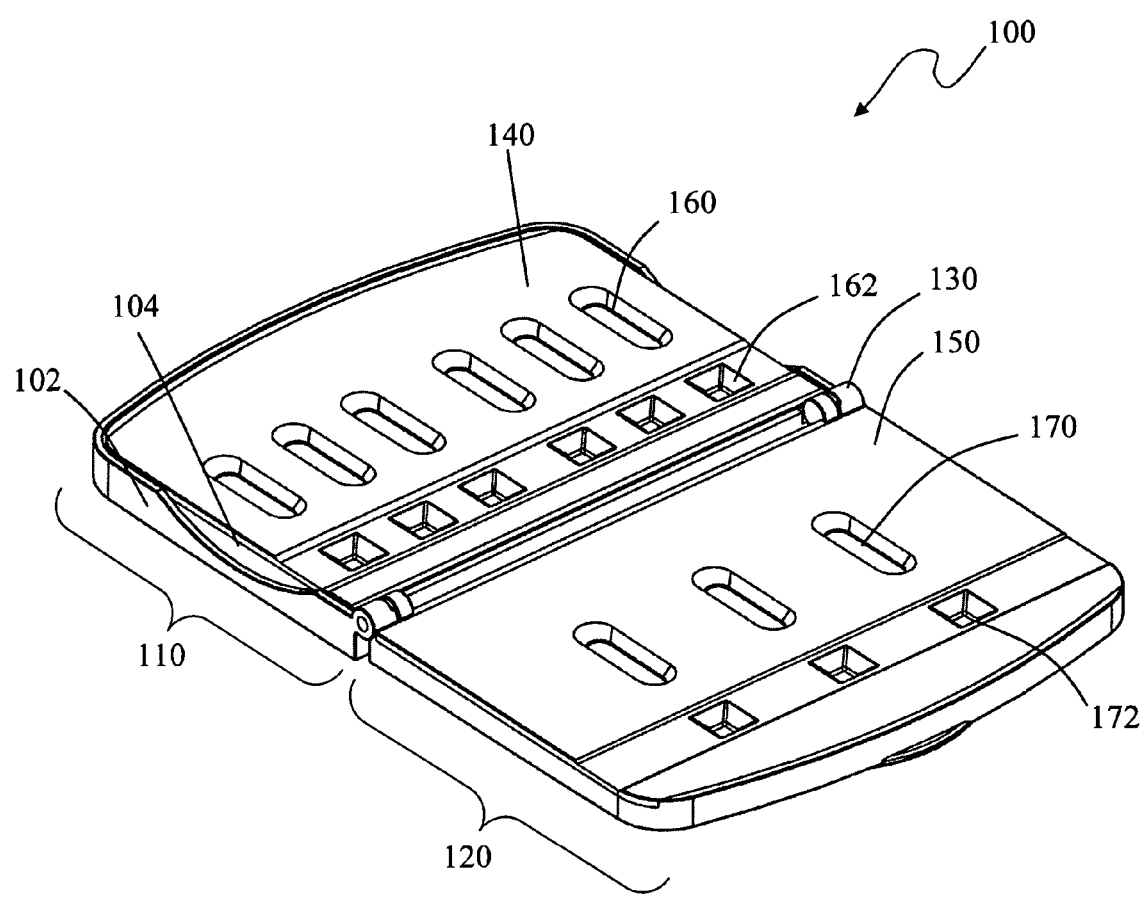

FIG. 1 depicts one embodiment of the present device. FIG. 1 shows a, bi-fold test device in an open position, illustrating the test face of the device. In this embodiment, one or more control lanes are located on the first panel 110 of the test device. Similarly, one or more sample test lanes are located on the second panel 120 of the test device. The test device is used in this open position.

Figure 2:
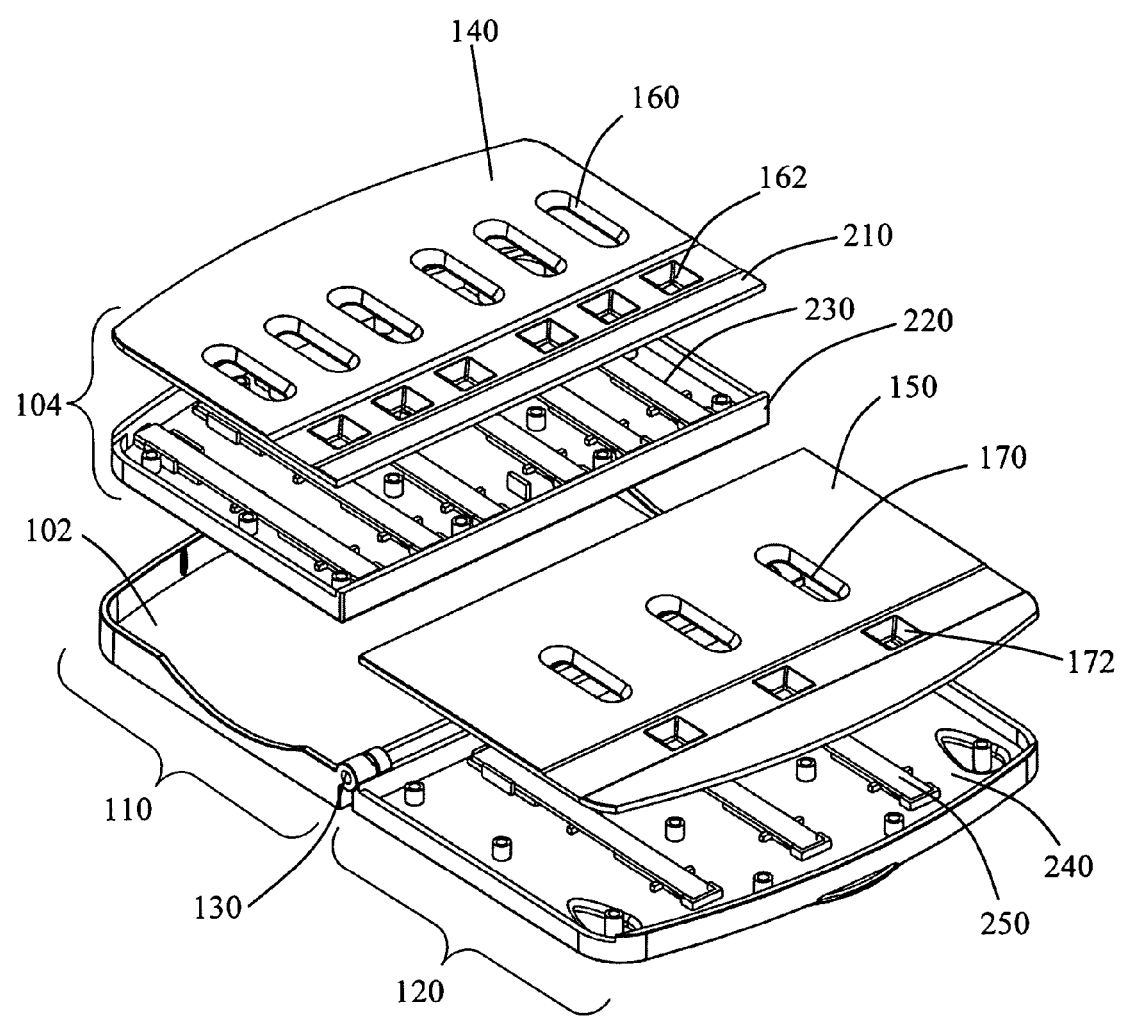

FIG. 2 is an exploded view of the embodiment of the instant device illustrated in FIG. 1.

Figure 3:
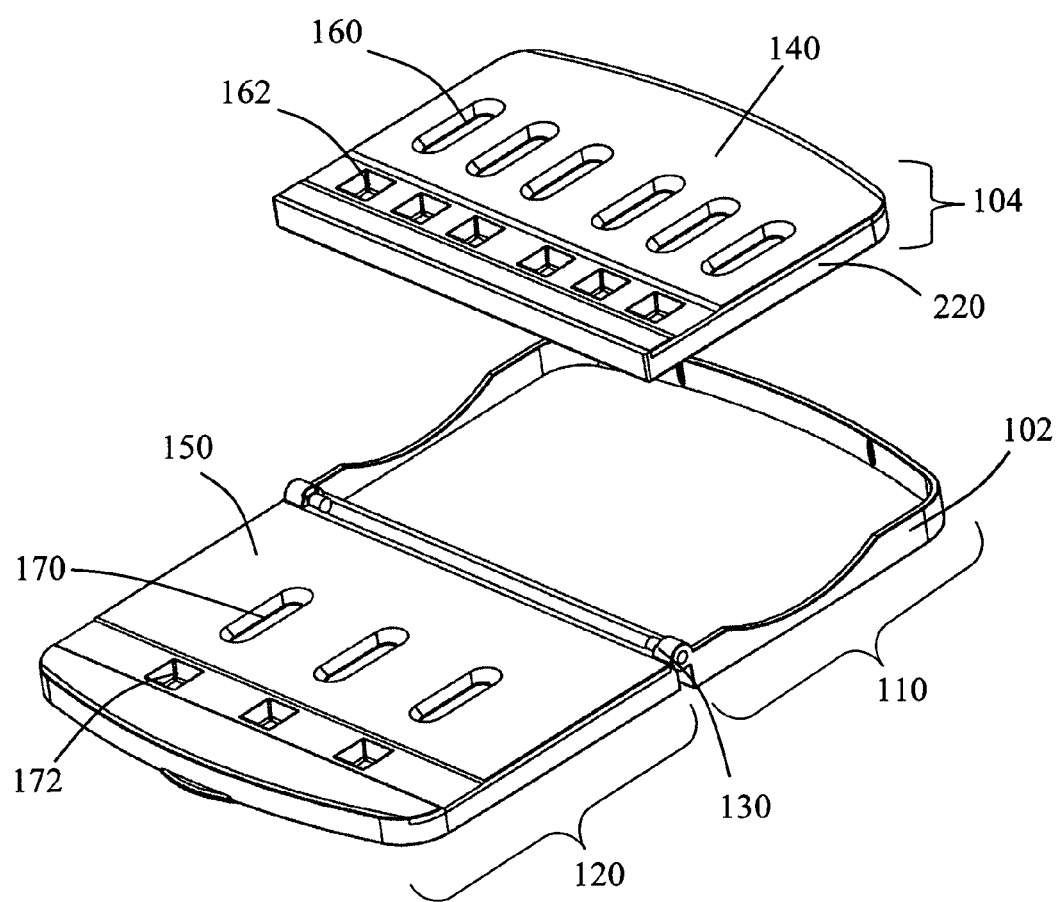

FIG. 3 illustrates one embodiment how the control cassette 104 fits into the top cover 102 of the first panel 110 of the device shown in FIG. 1.

Figure 4:
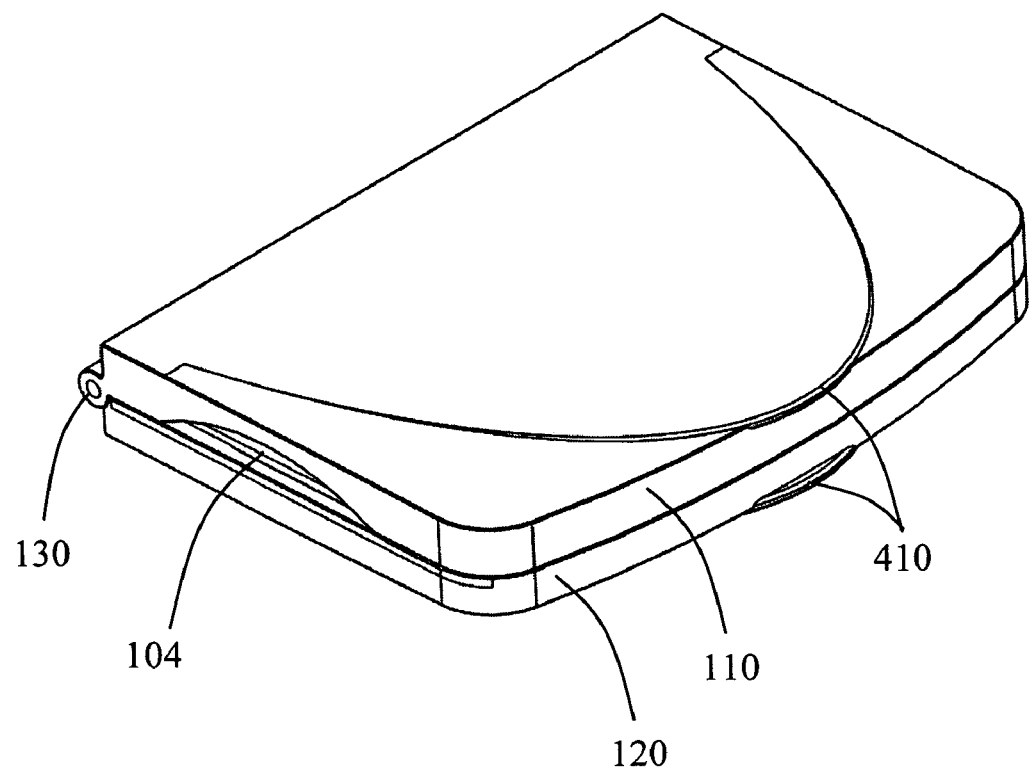

FIG. 4 shows the device of FIG. 1 in a closed position.

Figure 5:
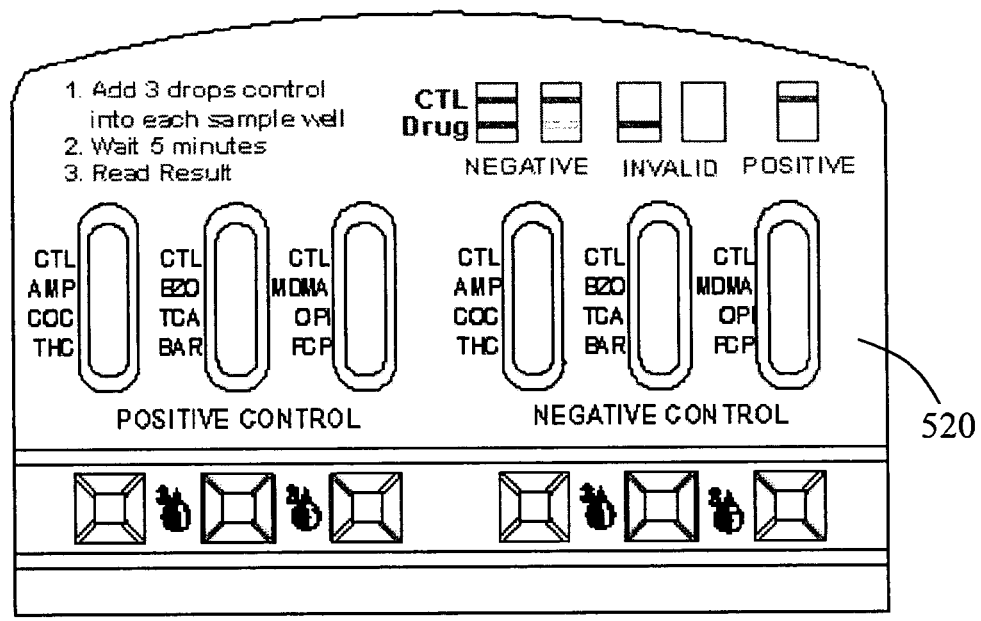
Figure 5:
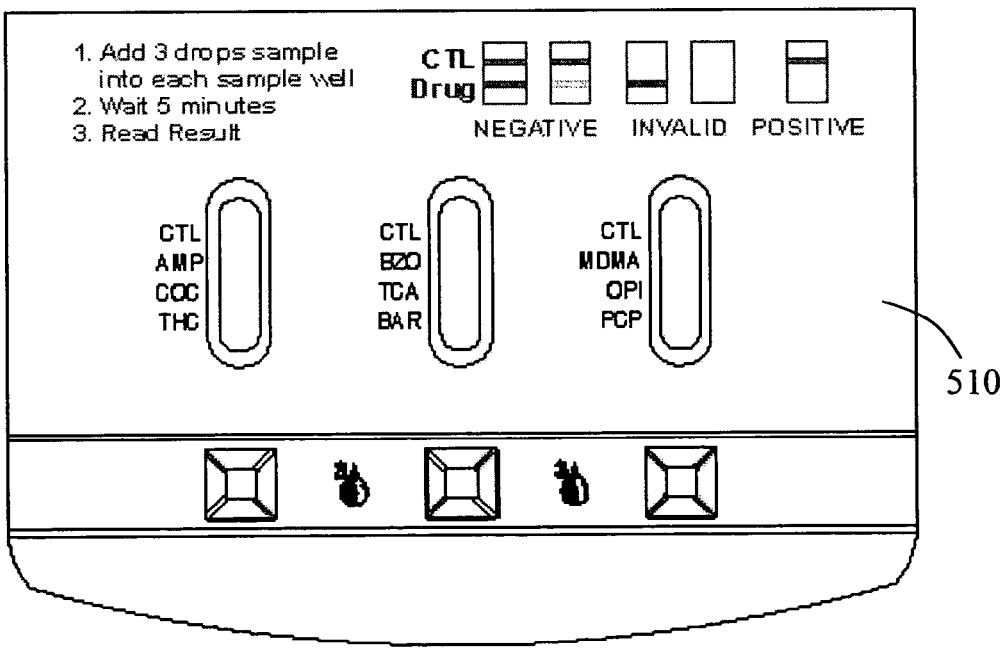

FIG. 5 shows one example of indicia which might be used on the test face of the device illustrated in FIG. 1. For example, control indicia 520 may appear on the face of the first panel 110. In another example, test indicia 510 may appear on the second panel 120.

Figure 6:
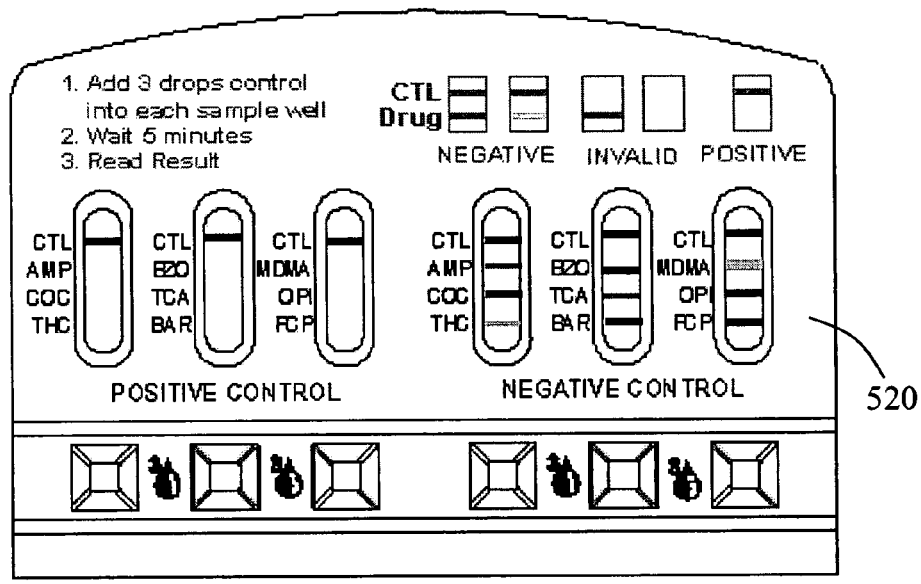
Figure 6:
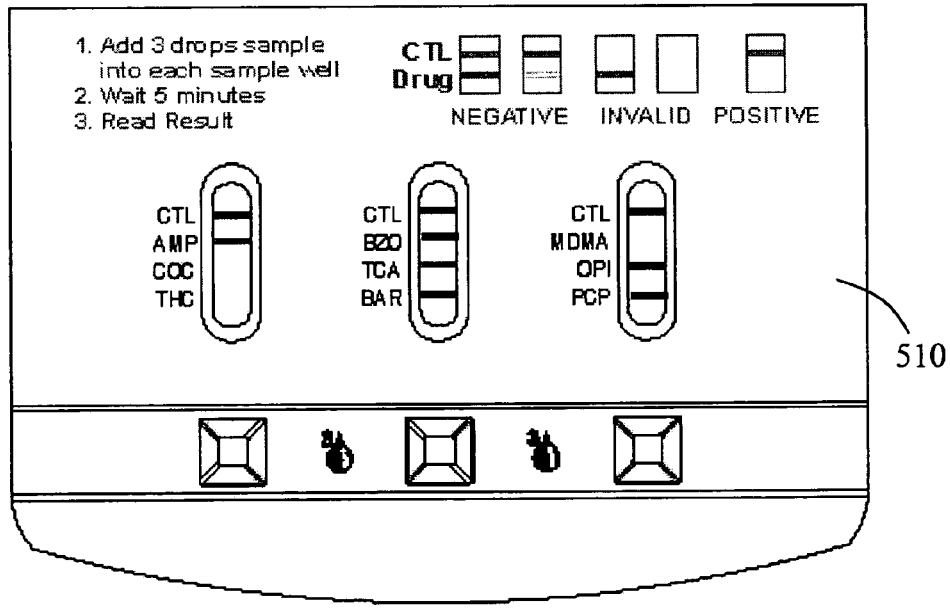

FIG. 6 is an example of what control and test results might look like if the subject providing the test sample had been using cocaine, pot and ecstasy.

Figure 7:
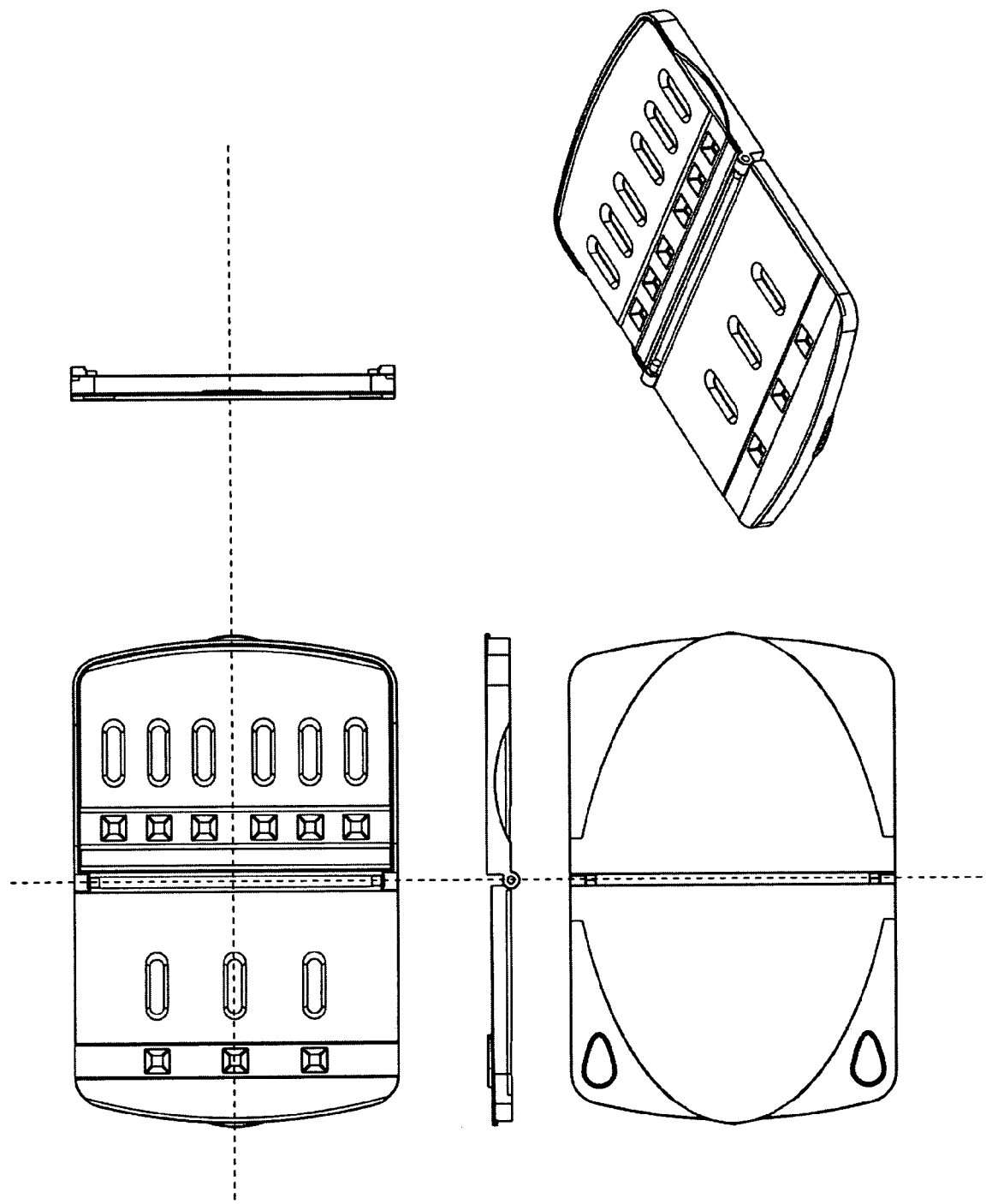

FIG. 7 illustrates various sides of the device of FIG. 1.

Figure 8:
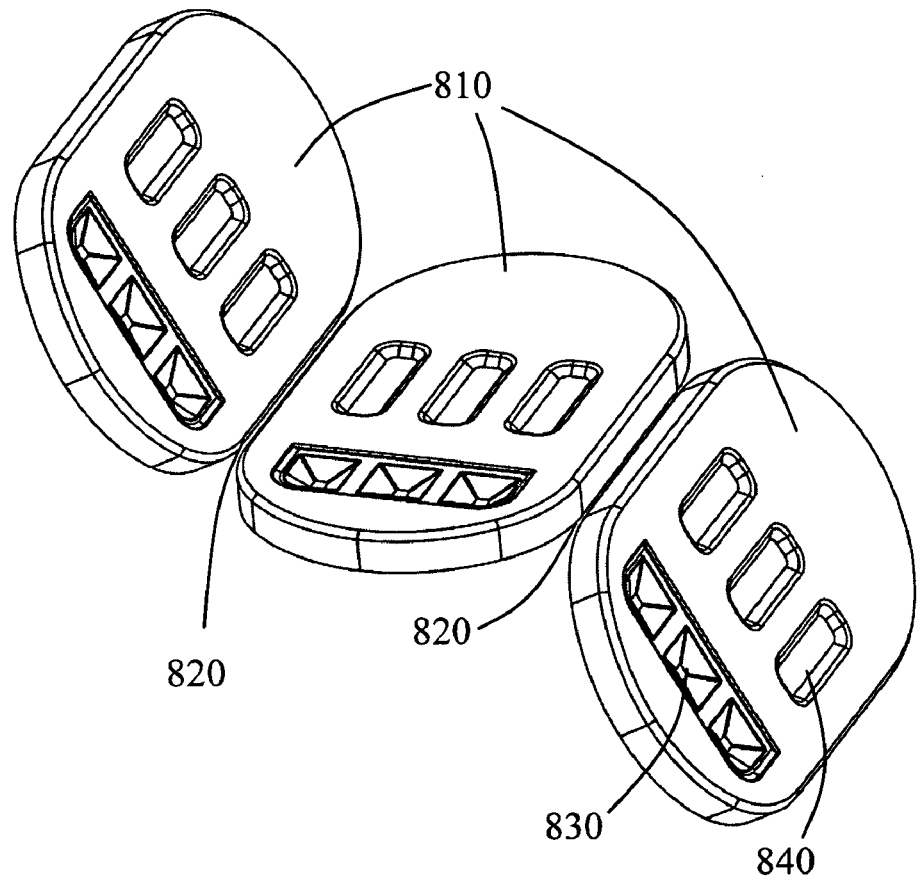

FIG. 8 illustrates another embodiment of the present device, a tri-fold test device, in a partially opened position.

Figure 9:
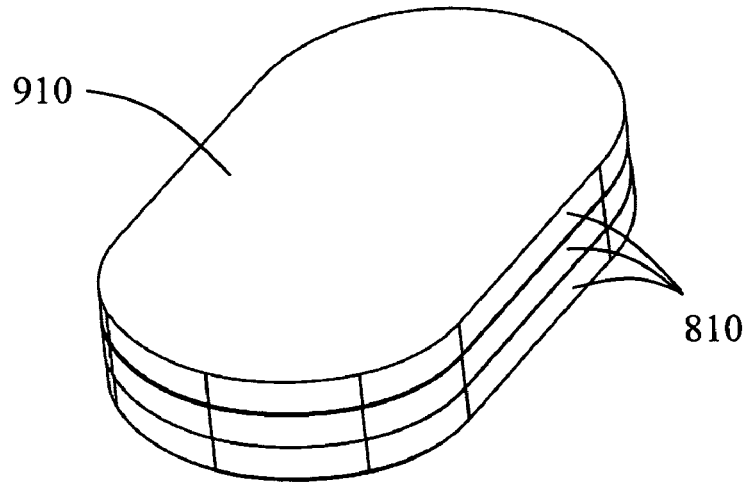

FIG. 9 shows the embodiment of FIG. 8 in the closed position.

DETAILED DESCRIPTION

Definitions

Unless defined otherwise, all technical and scientific terms used herein have the same meaning as commonly understood by one of ordinary skill in the art. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of the parts during use of the device. Where a term is provided in the singular, the inventors also contemplate the plural of that term. The nomenclature used herein and the laboratory procedures described below are those well known and commonly employed in the art. As employed throughout the disclosure, the following terms, unless other wise indicated, shall be understood to have the following meanings:

"Assaying" denotes testing for or detecting the presence of a substance or material, such as, but not limited to, a chemical, an organic compound, an inorganic compound, a metabolic product, a drug or a drug metabolite, an organism or a metabolite of such an organism, a nucleic acid, a protein, or a combination thereof. Optionally, assaying denotes measuring the amount of the substance or material. Assaying further denotes an immunological test, a chemical test, an enzymatic test, and the like.

A "reagent" can be any chemical, including organic compounds and inorganic compounds and combinations thereof. A reagent can be provided in gaseous, solid, or liquid form, or any combination thereof, and can be a component of a solution or suspension. A reagent preferably includes fluids, such as buffers useful in methods of detecting analytes in a sample or specimen, such as anticoagulants, diluents, buffers, assay reagents, specific binding members, detectable labels, enzymes and the like. A reagent can also include an extractant, such as a buffer or chemical, to extract an analyte from a sample or specimen or a sample collection device. For example, a buffer can be used to extract analytes from the sample or specimen, such as LPS from bacteria.

An "analysis device" or "assay device" is a device for analyzing a sample or specimen. An analysis device can be used to detect the presence and/or concentration of an analyte in a sample or specimen, or to determine the presence and/or numbers of one or more components of a sample or specimen, or to make a qualitative assessment of a sample or specimen. Analysis devices of the present disclosure include but are not limited to lateral flow detection devices such as assay strip devices, and columns.

A "lateral flow detection device" or a "lateral flow test device" is a device that determines the presence and/or amount of an analyte in a liquid sample or specimen as the liquid sample or specimen moves through a matrix or material by lateral flow or capillary action, such as an immunochromatographic device. A lateral flow detection device may be used in a substantially vertical or a substantially horizontal orientation or in an orientation substantially between vertical and horizontal. Persons knowledgeable in the art commonly refer to a lateral flow detection device using terms such as "immunochromatographic," "dip sticks," "membrane technology" and "test strips."

"Analyte" is the compound or composition to be measured that is capable of binding specifically to a ligand, receptor, or enzyme, usually an antibody or antigen such as a protein or drug, or a metabolite, the precise nature of antigenic and drug analytes together with numerous examples thereof are disclosed in U.S. Pat. No. 4,299,916 and U.S. Pat. No. 4,275,149. Analytes can include antibodies and receptors, including active fragments or fragments thereof. An analyte can include an analyte analogue, which is a derivative of an analyte, such as, for example, an analyte altered by chemical or biological methods, such as by the action of reactive chemicals, such as adulterants or enzymatic activity. An analyte may be a drug or drug metabolite, especially, but not limited to drugs of abuse, such as, for example amphetamines (speed), cocaine, THC (cannabis/pot), opiates (heroine), phencyclidine (PCP), methadone, benzodiazepines, methamphetamines (MDMA/ecstasy), phencyclidine (PCP/angle dust), tricyclic antidepressants and barbiturates.

An "antibody" is an immunoglobulin, or derivative or fragment or active fragment thereof, having an area on the surface or in a cavity, which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

"Sample" or "specimen" may be used interchangeably. "Sample" or "specimen" denotes any material to be assayed for the presence and/or concentration of an analyte in a sample or specimen, or to determine the presence and/or numbers of one or more components of a sample or specimen, or to make a qualitative assessment of a sample or specimen. A sample can be the same as a specimen. Preferably, a sample is a fluid sample, preferably a liquid sample. Examples of liquid samples that may be assayed using an assay device of the present disclosure include bodily fluids including blood, serum, plasma, saliva, urine, ocular fluid, semen, and spinal fluid; water samples, such as samples of water from oceans, seas, lakes, rivers, and the like, or samples from home, municipal, or industrial water sources, runoff water or sewage samples; and food samples, such as milk or wine. Viscous liquid, semi-solid, or solid specimens may be used to create liquid solutions, eluates, suspensions, or extracts that can be samples. For example, throat or genital swabs may be suspended in a liquid solution to make a sample. Samples can include a combination of liquids, solids, gasses, or any combination thereof, as, for example a suspension of cells in a buffer or solution. Samples can comprise biological materials, such as cells, microbes, organelles, and biochemical complexes. Liquid samples can be made from solid, semisolid or highly viscous materials, such as soils, fecal matter, tissues, organs or other samples that are not fluid in nature. For example, these solid or semi-solid samples can be mixed with an appropriate solution, such as a buffer, such as a diluent or extraction buffer. The sample can be macerated, frozen and thawed, or otherwise extracted to form a fluid sample. Residual particulates can be removed or reduced using conventional methods, such as filtration or centrifugation.

A "control" is a portion of the assay designed to determine various aspects of progress of the assay conducted on a sample of a subject. For example, one might want to determine if the assay ran correctly, if the assay gave a correct answer, if the assay is complete, and the like. In some cases, a control is designed to provide an example of a positive or negative result, to which the person running the assay can compare the results obtained from assaying the sample of the subject. Controls may be run in various ways, which are well known in the art, depending upon the purpose of the control. For example, procedural controls generally indicate that the assay is complete. More specifically, in an immunoassay test strip, a control line may appear at the end of the test zone, to indicate that the sample has run far enough in the test strip and that the assay has been conducted for a long enough time. In another example, "reactive controls" may be run. Reactive controls may comprise extra lines on the test strip that mimic what the test result lines would look like if the test is either positive or negative, depending upon if the reactive control is either a positive or negative reactive control line. Generally, reactive controls are not considered to be true positive or negative controls. In yet another example, controls may be positive or negative. In the art, they may be referred to as "true positive controls" or "true negative controls," in order to differentiate this type of control from the procedural or reactive controls. In the example of true positive and negative controls, two extra test strips are used, in addition to the test strip used to assay the subject sample. Positive and negative control solutions are also provided to the user. The positive control solution is similar to the sample solution and is spiked with a defined amount of the analyte of interest, or an analogue thereof, for which the subject sample will be assayed. The positive control solution will be applied to one of the test strips and will react with the appropriate reagents on the test strip to produce a positive test result. The negative control solution is substantially the same as the positive control, except that the negative control solution is not spiked with the analyte of interest. The negative control solution is applied to a second test strip. The negative control solution produces a negative result. The subject sample would be applied to the third test strip, in parallel with the positive and negative controls being applied to their respective test strips as described above. At the conclusion of the assay, the assay results of the subject sample could be compared to the assay results of the positive and negative tests, to confirm the positive or negative results of the assay of the subject sample.

Other technical terms used herein have their ordinary meaning in the art that they are used, as exemplified by a variety of technical dictionaries.

Assay Device

In the drug of abuse testing industry, various governmental agencies and professional organizations, such as but not limited to CLIA CAP, COLA and JCCHO, have initiated regulations to ensure quality control and standardization of testing with point of care devices. For example, these agencies and organizations may require certain positive, negative or procedural controls to be run at the beginning of the day, or the beginning of a new lot of devices. No point of care test devices currently on the market have true positive and negative controls, to which the test results obtained with the test sample can be compared, creating an ongoing and existing need. The present disclosure recognizes and provides a solution to this clear and ongoing need. In particular, the present device comprises on-board true positive and optionally true negative controls. More preferred, the present device comprises both on-board true positive and true negative controls. Most preferred, the present device comprises on-board true positive and true negative controls, having true positive and true negative control solutions. These positive and/or negative controls are assayed at the same time as the test sample, and the results of the test sample assay can be directly compared to the results of the positive and/or negative control assays, to ascertain if the test assay functioned correctly, the assay was conducted correctly, and/or if the results of the test sample assay were interpreted correctly.

Referring now to the figures, FIGS. 1 through 4 illustrate one embodiment of the present device, a test device 100 for detecting the presence of an analyte of interest in a liquid sample, such as, for example, urine or blood. FIGS. 1, 2 and 3 show the test device in the open position. FIG. 4 shows the test device in the closed position, showing thumb tabs 410. FIG. 2 and FIG. 3 are various explosions of the embodiment depicted in FIG. 1 and help to illustrate the assembly of the device of FIG. 1. The structural characteristics of the present device will be described below. Then the function of the present device will subsequently be described.

FIG. 1 is a cartoon of one embodiment of the present device 100, in the open position. The device comprises two or more panels 110, 120 that are movably attached, so that the device can be opened and closed. In the embodiment shown in FIG. 1, there are only two panels, a first panel 110 and a second panel 120. The first panel 110 and second panel 120 are movably attached to each other, for example, but not limited to, by a hinge 130. It should be appreciated that the quantity of panels can vary.

In certain embodiments of the present device, more than two panels may be attached using various attachment methods. For example, FIGS. 8 and 9 show a triple panel that closes by an accordion fold 820. Various means, such as hinges, may be used to connect the panels and make it possible to open and close the device. In this embodiment of the present device, each panel 810 has one or more application wells 830 and one or more result windows 840. Various aspects of sample and control arrangement are contemplated by the inventors. In one aspect, for example, the sample test strips may all be on one panel 810, all of the positive controls on a second panel 810, and all of the negative controls on a third panel. In an alterative aspect of the present device, one sample test strip, one positive control test strip and one negative control test strip may be arranged on each panel. Alternative arrangements of the sample and control test strips may also be used.

The housing of the present device can be manufactured with various materials. These materials can include but are not limited to metal, silicon, glass, ceramic, plastic and synthetic and natural polymers or any combination thereof. In one embodiment of the device, the housing can be manufactured from a polypropylene composite using an appropriate manufacturing method such as pressure injection molding or machining. Methods of manufacturing the housing can include but are not limited to milling, casting, blowing, and spinning.

As shown in FIG. 2, a panel may be constructed a variety of ways. As an example, two preferred panel structures will be discussed. For convenience and clarity, the two types of structures will be referred to as "Insert Panel" and "Plain Panel." In FIGS. 1 and 2, the "Insert Panel" structure is illustrated by the first panel 110 of the present device. In contrast, the "Plain Panel" structure is characterized by the second panel 120. For simplicity, each type of panel structure will be dealt with in turn.

Insert Panel Structure

As discussed above, certain embodiments of the present device comprise panels having an "insert structure" (see FIGS. 1, 2 and 3). The first panel 110, of the embodiment of the present device shown in FIGS. 1 and 2, has and "insert structure." As shown in the figures, the first panel 110 further comprises a first cover 102 and an insert 104 that fits snuggly into the first cover 102. The use of inserts can facilitate the large scale manufacture, as separate portions of the device may be assembled separately and later put together in the final configuration. In additional embodiments of the present device, the insert 104 further comprises an insert face 140 and an insert back 220. The insert face 140 has one or more insert result windows 160 as well as an identical number of insert application wells 162. The insert face 140 and insert back 220 are fabricated so as to attach to each other to form a cassette that can hold test strips 230. The insert face 140 and insert back 220 may be attached together by any convenient means, such as snapping, gluing or welding them together. As shown in FIG. 2, the insert back 220 may contain structures that hold the test strips 230 in the correct location and orientation.

As discussed above, in certain embodiments of the present device, the insert 104 comprises one or more test strips 230. The number of test strips 230 is the same as the number of results windows 160 and application wells 162 on the insert face 140. For example, FIG. 2 shows and insert containing six test strips 230, each with corresponding results windows 160 and application wells 162. In the illustrated embodiment (see FIG. 2), three of the test strips 230 are dedicated to positive controls. The remaining three test strips 230 are used for negative controls.

As shown in the example illustrated in FIG. 1, the insert face 140 of the first panel 110 has control solution wells 162 and control result windows 160. FIG. 2 shows that the wells 162 and result windows 160 line up with the corresponding portion of the test strip 230 below. For example, the well 162 lines up with a sample application zone on the test strip 230 below. Similarly, the result window 160 lines up with the result zone of the test strip 230 below.

Plain Panel Structure

As discussed above, certain embodiments of the present device comprise panels having an "insert structure" (see FIGS. 1, 2 and 3). The second panel 120, of the embodiment of the present device shown in FIGS. 1 and 2, has a "plain panel structure." In additional embodiments of the present device, a panel 120 may comprise a back cover 240 and a face plate 150. In this arrangement, the inner surface of the back cover 240 may have structures designed to hold a test strip 250 in the correct orientation for use. The face plate 150, as shown in the present example, has one or more face plate application wells 172 and face plate result windows 170. The face plate application wells 172 and face plate result windows 170 align with the test strips 250, below the face plate 150. Thus, a liquid sample may easily be applied to the sample application zone of the test strips 250 and the results of the assay may be viewed through the results windows 170.

Test Strip Arrangements

FIG. 2 shows that each panel 110 and 120, of the present device, further comprises one or more test strips 230, 250. Additionally, each panel 110, 120 comprises a face plate 140, 150 having sample application wells 162, 172 and result windows 160, 170. The sample application wells 162, 172 and result windows 160, 170 are aligned with the test strips 230, 250 below them. Depending upon the nature of the tests to be conducted, the analyte test strips may be grouped together, the positive controls may be grouped together and the negative controls may be grouped together. Alternatively, the analyte test strips may each be grouped together with their respective positive and negative controls. While the present disclosure contemplates various strip arrangement schemes, the arrangements of test and control strips chosen should facilitate the maximum ease of use and clarity of results.

Indicia

Indicia may be used to instruct the user how to perform the test and interpret the results. It should be appreciated that various types of indicia can be used, and that the indicia is not limited to alpha-numeric characters. In the embodiment shown in FIG. 5, the tests are arranged so that the controls 520 are grouped together on a first panel and the sample assay tests 510 are grouped together on a second panel. Further in this example, the positive controls are on the left-hand side to the first panel, with each test strip testing for 3 drugs (denoted by AMP, COC, and THC; BZO, TCA and BAR; and MDMA, OPI and PCP) and a procedural control (denoted by CTL). As indicated below each positive control results window, three drops of the positive control solution should be placed in the positive control wells. Similarly, the negative controls are grouped on the right-hand side to the first panel. The indicia next to negative control results windows are the same as those next to the positive control results windows. However, the indicia below the negative control result window tell the user that they should add 3 drops of the negative control solution to the negative control wells. The sample assay test result windows, on the second panel, are labeled in the same manner as the positive and negative control windows (above). Here, three drops of the sample, such as urine or blood from a patient, are added to each sample application well.

FIG. 6 shows what test results might look like, following the procedures for testing a sample for the presence of drugs of abuse. In this example, the assays conducted (except for the procedural controls, CTL) are competitive immunoassays. This means that a line appears when the test is negative. If the test is positive for a drug, no line will appear where one should be, according to the indicia next to the results windows. Accordingly, all of the positive controls shown in FIG. 6 have no lines. Further, negative control test results appear as bands or lines, possibly of varying intensity or width, in the negative control result windows.

An example of sample test results are shown in the second panel (lower half of FIG. 6). In this example, there is no line for COC, THC or MDMA. But, there are lines for AMP, BZO, TCA, BAR, OPI and PCP. A technician testing a person's urine for the presence of drugs of abuse would interpret these test results to indicate that the person giving the urine sample had used cocaine (COC), pot (THC) and ecstasy (MDMA) recently.

Unlike the true positive and negative controls, the procedural controls (CTL) are sandwich immunoassays to an analyte unrelated to the analyte(s) of interest. Therefore, the procedural controls (CTL) produce a line for a positive result. Furthermore, no line is produced for a negative procedural control result. The procedural control (CTL) simply indicates if the applied sample or control solution ran a far enough distance through the test strip.

Test Strips

The test strips used in the disclosed device can be of any assay element known in the art and preferably comprises at least one lateral flow detection device such as an assay strip or test strip. Such lateral flow detection devices include, but are not limited to: immunoassays, chemical assays and enzymatic assays commonly known in the art, such as but not limited to, single antibody immunoassays, multiple antibody immunoassays, sandwich immunoassays, competitive immunoassays, non-competitive immunoassays and the like, including assays that utilize horseradish peroxidase, alkaline phosphatase, luciferase, antibody conjugates, antibody fragments, fluorescently tagged antibodies, modified antibodies, labeled antibodies, antibodies labeled with colloidal gold, antibodies labeled with colored latex bead, and the like, which are commonly known in the art. Examples of some assay strips that can be incorporated into the present device can be found in the following US patents: U.S. Pat. No. 4,857,453; U.S. Pat. No. 5,073,484; U.S. Pat. No. 5,119,831; U.S. Pat. No. 5,185,127; U.S. Pat. No. 5,275,785; U.S. Pat. No. 5,416,000; U.S. Pat. No. 5,504,013; U.S. Pat. No. 5,602, 040; U.S. Pat. No. 5,622,871; U.S. Pat. No. 5,654,162; U.S. Pat. No. 5,656,503; U.S. Pat. No. 5,686,315; U.S. Pat. No. 5,766,961; U.S. Pat. No. 5,770,460; U.S. Pat. No. 5,916,815; U.S. Pat. No. 5,976,895; U.S. Pat. No. 6,248,598; U.S. Pat. No. 6,140,136; U.S. Pat. No. 6,187,269; U.S. Pat. No. 6,187,598; U.S. Pat. No. 6,228,660; U.S. Pat. No. 6,235,241; U.S. Pat. No. 6,306,642; U.S. Pat. No. 6,352,862; U.S. Pat. No. 6,372,515; U.S. Pat. No. 6,379,620; and U.S. Pat. No. 6,403,383. Further examples of some assay strips that can be incorporated into the present device can be found in the following U.S. patent applications Ser. Nos. 09/579,672; 09/579,673; 09/653,032; 60/233,739; 09/915,494, 10/211,199 and 09/860,408.

Specimen

Any type of liquid specimen may be used with the present device, including liquid specimens of the nature and character as described above in the definition portion of this disclosure. Alternatively, the sample applied to the test strip of the present device may be derived from other types of specimens dissolved in an appropriate liquid, such as a buffer or water. For example, the specimen may be composed of fine powdery materials such as talc, carbon black, pharmaceutical preparations, or gases such as argon or methane. Additional specimens can include atmospheric specimens that can be assayed for particulates or radioactive isotopes such as radon.

In an alternative embodiment of the present device the specimen to be tested is a biological specimen. Such biological specimens include but are not limited to a sample from a subject such as an animal or a human. A sample from a subject can be of any appropriate type, such as a sample of fluid, tissue, organ or a combination thereof. The biological specimen can also be a sample of other biological material, such as plants, bacteria, cell or tissue cultures, viruses and prions, or food, including food such as material derived from plants or animals or combinations thereof. The sample can be processed prior to introduction into the assay device. In the alternative, a sample and reagent can be combined within a specimen collection container. Such reagents can be used to process a sample, such as digesting solid samples with appropriate reagents such as chemicals, such as acids or bases, or with enzymes such as proteases. Other reagents can be used to extract analytes from a sample, such as extraction of antigens from biological entities, such as antigens from etiological agents such as bacteria, parasites, viruses or prions such as known in the art.

The specimen can also be an environmental sample, such as a sample of soil, water, wastewater, landfill or landfill leachate.

While a number of different biological specimens are suitable for collection by the specimen collection container, commonly collected specimens are biological samples, including but not limited to fluid sample including urine, blood, serum, saliva, and semen, secretions including vaginal secretions, central nervous system fluids, lavages and the like.

Methods of Use

The present disclosure contemplates methods of use of the test device described supra. One embodiment of a present method for detecting an analyte of interest in a sample of a subject in need there of, comprises the following steps. First a sample, such as urine or blood, is collected from a subject. A test device of the present disclosure, such as one describe supra, is provided and an aliquot of the sample is applied to the sample wells of the test device. Next an aliquot of the positive control solution is applied to the positive control wells and an aliquot of the negative control solution is applied to the negative control wells. The test device is then incubated for an appropriate amount of time. The amount of time necessary to incubate the device is dependent upon the length of the test strips, the test strip design and components, and the characteristics of the subject sample used. However, since the consumer wants rapid results, the tests are usually designed to take only a few minutes to run. At the conclusion of the incubation period, the operator of the test can read the test results and compare the test results to the positive and negative control results. After reading the test results and confirming the correct functioning of the test device by comparing the test results to the positive and negative control results, the operator would report the results where and when appropriate, and dispose of the test device.

KITS

Another embodiment of the present disclosure is a test kit, for testing a sample for the presence of an analyte, such as drugs of abuse or metabolites. In preferred embodiments, the test kit comprises a test device of the present disclosure, as described supra, control solutions and instructions describing the correct use of the device. Different types of kits are contemplated by the present disclosure. For example, the needs of an employment drug testing site may be different from the needs of a doctor's office. The kit can be tailored to meet those needs. For example, kits purchased by an employment drug testing site may contain 20 test devices, 10 ml dropper bottles of the positive and negative control solutions and one set of instructions. In such a setting, the emphasis is on high through-put and one or two technicians would perform many tests each day. In this situation, the technicians could share the control solutions and might only read the instructions the first time that they used one of the devices.

In contrast, a doctor's office might use one of the test devices on an infrequent basis. In such a situation, different people might conduct the tests and need single devices packaged together with small dropper bottles containing only enough control solutions necessary for one device. In this kind of situation, it may be preferred to supply instructions packaged with each device and set of control solutions.

EXAMPLES OF USE

Drug Testing Prior to Employment

A manufacturing company has conditionally hired a new engineer. Prior to the first day of work, the engineer goes to a drug testing laboratory, where he is tested for illegal drugs. At the drug testing laboratory, the engineer produces a urine sample for the technician and then leaves the facility. The technician takes a drug of abuse test device of the present disclosure, opens it and places it on the bench top. Next, using a disposable transfer pipette, the technician applies three drops of the engineer's donated urine to each sample application well of the test device. Then she squeezes three drops of positive control solution, from the positive control solution squeeze bottle, into each positive control well. Similarly, she squeezes three drops of negative control solution, from the negative control solution squeeze bottle, into each negative control well. She sets a timer for five minutes and allows the test device to incubate on the bench top. At the conclusion of the incubation, the technician reads and records the test and control (positive and negative) results for each drug assayed. When she is finished, the technician disposes of the remaining urine and the used test device, and mails the results to the employer.

Bedside Drug Overdose Testing in the Emergency Room

In the emergency room, an unconscious teenager is brought in. Due to his vital signs, the doctors suspect that the teenager has been taking drugs. To determine what drugs the teenager has taken, the nurse obtains a test device of the present disclosure, pricks the teenager's finger with a lancet, removes a small amount of his blood, and applies the blood to the sample wells of the test device. Then the nurse applies a small amount of the included control solutions to the appropriate wells of the test device. After a short incubation period, the nurse reads the test results and determines that the teenager has over-dosed on ecstasy. The nurse reports the results to the doctors, who proceed with the appropriate ecstasy overdose treatment for the teenager.

We claim:

1. A test device for detecting an analyte in a sample, comprising:
    at least two panels hingeably attached to each other and having an open position and a closed position, the panels having interior and exterior surfaces, wherein the interior surfaces of at least two of the panels directly face each other when the device is in the closed position,
    wherein each panel comprises at least one test strip for detecting the analyte; and
    wherein at least one of the panels is an insert panel and comprises an insert structure comprised of a cassette that contains at least one test strip and wherein the insert panel has a cavity that opens toward an adjacent panel when the device is in the closed position and wherein the insert structure comprises a structure removably positioned in the cavity.

2. The device of claim 1 wherein the insert structure contains at least one test strip for detecting the presence of an analyte selected from the group consisting of amphetamines, cocaine, THC, opiates, phencyclidine, methadone, bezodiazepines, methamphetamines, tricyclic antidepressants, and barbiturates.

3. The device of claim 1 wherein the interior surface of each panel further comprises at least one application well for the application of the sample, a true positive control or a true negative control, wherein each application well has an opening that opens toward an adjacent panel when the device is in the closed position.

4. The device of claim 3, wherein the application well is in fluid communication with the test strip.

5. The device of claim 1, wherein the interior surface of each panel further comprises a window for observing a test result.

6. The device of claim 5, wherein the test result can be visually determined.

7. The device of claim 1, wherein the test strip comprises
    a reagent zone comprising reagents for conducting the assay;
    a label zone comprising reagents for detecting the analyte; and
    a detection zone comprising reagents for detecting the analyte.

8. The device of claim 7, wherein the reagent zone and the label zone are the same.

9. The device of claim 7, wherein the detection zone comprises specific binding molecules immobilized on the test strip.

10. The device of claim 1, the test strip further comprising a chemical test.

11. The device of claim 1, the test strip further comprising an immunoassay.

12. The device of claim 1, wherein the sample is a biological sample.

13. The device of claim 1, wherein the sample is a liquid or a solution comprising a biological sample.

14. The device of claim 1, wherein the sample is selected from the group consisting of blood, plasma, saliva, oral fluid, cerebrospinal fluid, urine, fecal material, mucous, vaginal or oral swabs, semen, tissue, fluid or puss exudates, aspirates, cell culture, conditioned media from a cell culture, homogenized cell culture, homogenized tissue and solutions derived from solid or semi-solid biological samples.

15. The device of claim 1, wherein the analyte is selected from the group consisting of drugs, drugs of abuse, alcohol, poisons, bacteria, viruses, proteins, sugars, carbohydrates, lectins, fats, antibodies, receptors, hormones, etiological agents and biological metabolites.

16. The device of claim 3, wherein the true positive control comprises the analyte and a buffer.

17. The device of claim 3, wherein the true negative control comprises a buffer and does not comprise the analyte.

18. The device of claim 1, wherein the insert structure fits snuggly into the cavity of the insert panel.

19. The device of claim 1, wherein the cassette comprises a face structure that removably mates with a back structure, wherein the face structure faces an adjacent panel when the device is in the closed position.

20. The device of claim 1, wherein the cassette includes at least one application well and at least one communication result window that communicate with at least one test strip contained in the cavity, wherein the at least one application well has an opening that opens toward an adjacent panel when the device is in the closed position.

* * * * *